United States Patent
Van Der Linden et al.

(10) Patent No.: US 7,301,038 B2
(45) Date of Patent: Nov. 27, 2007

(54) PROCESS FOR PREPARING ALKYLENE OXIDE (EPOXID, OXIRANE)

(75) Inventors: Johannes Petrus Van Der Linden, Amsterdam (NL); Ingmar Hubertus Josephina Ploemen, Amsterdam (NL); Augustinus Santen, Rijswijk (NL); Alexander Jan Van Der Veen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 224 days.

(21) Appl. No.: 10/477,060

(22) PCT Filed: May 3, 2002

(86) PCT No.: PCT/EP02/04970

§ 371 (c)(1), (2), (4) Date: May 3, 2004

(87) PCT Pub. No.: WO02/090340

PCT Pub. Date: Nov. 14, 2002

(65) Prior Publication Data

US 2004/0210067 A1 Oct. 21, 2004

(30) Foreign Application Priority Data

May 8, 2001 (EP) .................. 01304132

(51) Int. Cl.
*C07B 301/03* (2006.01)
*C07B 301/19* (2006.01)
*C07B 301/12* (2006.01)

(52) U.S. Cl. .................. 549/524; 549/529; 549/531
(58) Field of Classification Search ............. 549/524, 549/529, 531
See application file for complete search history.

(56) References Cited

U.S. PATENT DOCUMENTS

| | | | |
|---|---|---|---|
| 4,367,342 A | | 1/1983 | Wulff et al. |
| 5,849,937 A | | 12/1998 | Jubin, Jr. et al. |
| 6,066,750 A | * | 5/2000 | Chang .................. 549/524 |
| 6,365,761 B1 | * | 4/2002 | Derks et al. .......... 549/529 |

FOREIGN PATENT DOCUMENTS

| | | |
|---|---|---|
| EP | 0345856 | 8/1992 |
| EP | 1204653 | 5/2002 |
| WO | 98/18547 | 5/1998 |
| WO | 98/32530 | 7/1998 |
| WO | 99/01445 | 1/1999 |
| WO | 99/32472 | 7/1999 |
| WO | 01/05778 | 1/2001 |
| WO | 01/12617 | 2/2001 |
| WO | 01/72729 | 10/2001 |

OTHER PUBLICATIONS

International Search Report dated Jul. 9, 2002.

* cited by examiner

*Primary Examiner*—Thomas McKenzie
*Assistant Examiner*—Raymond Covington

(57) ABSTRACT

A process for the preparation of alkylene oxide, which process involves passing a feed containing an organic hydroperoxide and alkene through a bank of at least two serially connected reactors containing epoxidation catalyst and withdrawing a product stream having alkylene oxide and an alcohol as reaction products, in which bank of reactors the temperature of the feed is controlled such that during operation the outlet temperature of the final reactor is at least 4° C. higher than the outlet temperature of the first reactor.

20 Claims, No Drawings

1

PROCESS FOR PREPARING ALKYLENE OXIDE (EPOXID, OXIRANE)

FIELD OF THE INVENTION

The present invention relates to a process for the preparation of alkylene oxide.

BACKGROUND OF THE INVENTION

The epoxidation of alkene into alkylene oxide by reacting the alkene with an organic hydroperoxide is known in the art.

For instance, in the commonly known method for co-producing propylene oxide and styrene starting from ethylbenzene, the aforementioned epoxidation reaction is applied. In general this co-production process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl-ethanol, and (iii) converting the 1-phenyl-ethanol into styrene by dehydration using a suitable dehydration catalyst.

Another method for producing alkylene oxide is the coproduction of propylene oxide and methyl tert.-butyl ether (MTBE) starting from isobutane and propene. This process is well known in the art and involves similar reaction steps as the styrene/propylene oxide production process described in the previous paragraph. In the epoxidation step tert-butyl hydroperoxide is reacted with propene forming propylene oxide and tert-butanol in the presence of a heterogeneous epoxidation catalyst. Tert-butanol is subsequently etherified with methanol into MTBE, which is used as an additive in motor fuels.

U.S. Pat. No. 5,849,937 relates to an olefin epoxidation process using a plurality of reactor vessels each containing a fixed bed of a heterogeneous catalyst. When the activity of the catalyst in an individual reactor vessel falls to an undesirably low level, said reactor vessel is taken out of service and a replacement reactor vessel containing fresh or regenerated catalyst is introduced. The temperature of the feedstream is controlled such that the temperature does not exceed 125° C. In Comparative Example 1, the temperature of the feed to the reactor vessel is about 38° C. at the start of the epoxidation cycle and the heat-exchangers are initially by-passed. The temperature is gradually increased as necessary to maintain the desired level of conversion. At the end of the epoxidation cycle, the feed inlet temperature of the heat exchanger (and therefore the reactor outlet temperature) is 121° C. for each reactor.

As mentioned in U.S. Pat. No. 5,849,937, during operation the temperature of a bank of epoxidation reactors generally is increased in time to maintain the desired level of conversion which would otherwise decrease due to catalyst deactivation.

SUMMARY OF THE INVENTION

In the process according to the present invention, it has been found that better use can be made of the catalyst if the temperature of the reactors is increased according to a certain temperature profile.

A higher selectivity towards alkylene oxide can be obtained in a process for preparing alkylene oxide from organic hydroperoxide and alkene with the help of a bank of reactors by applying a specific temperature profile over the reactors. According to the present invention, the temperature of the feed should be such that during operation the outlet temperature of the final reactor is at least 4° C. higher than the outlet temperature of the first reactor and the average temperature of the first reactor should be lower than the average temperature of the final reactor.

Therefore, the present invention concerns a process for the preparation of alkylene oxide, which process comprises passing a feed containing an organic hydroperoxide and alkene through a bank of at least two serially connected reactors containing epoxidation catalyst and withdrawing a product stream comprising alkylene oxide and an alcohol as reaction products, in which bank of reactors the temperature of the feed is controlled such that during operation the outlet temperature of the final reactor is at least 4° C. higher than the outlet temperature of the first reactor and such that the average temperature of the first reactor is lower than the average temperature of the final reactor.

DETAILED DESCRIPTION OF THE INVENTION

In the present specification, a reactor is considered to be a reactor if it contains at least 5% wt of the total catalyst used in the process according to the present invention, preferably at least 7% wt.

The first reactor is the reactor which is first contacted by the feed in the process according to the present invention. It will be clear to someone skilled in the art that the feed can be pretreated in one or more reactors before being subjected to the process according to the present invention.

The final reactor is considered to be the reactor before which the alkylene oxide is separated off and which is in operation. If the conversion in the reactors in operation is sufficient, it is possible that no feed is passed through one or more reactors at the start of the operation. At the time when one or more reactors are taken into operation, the temperature profile of these reactors will be relatively rapidly brought into accordance with the present invention. In the present description, the reactors are described in the direction of flow of the feed.

The start of the operation is the time at which the catalyst in the first reactor is replaced by fresh catalyst. In many cases, the temperature profile at the start of operation will be different from the temperature profile during operation due to the fresh catalyst present and constrained cooling duties. The time at which the temperature profile will change from the profile at the start of operation to the profile during operation, will differ per case. However, "during operation" will generally be after at least one fifth of the life time of the catalyst has passed, preferably at least one quarter of the life time of the catalyst has passed, more specifically when at least one third of the life time of the catalyst has passed. The life time of the catalyst is the time during which the catalyst is being used in the process. After having been taken out of operation, catalyst will generally be regenerated and used again in the process of the present invention.

As stated, the first reactor contains fresh catalyst at the start of operation. Although the catalyst in all reactors can be replaced at the same time, in some instances it can be advantageous if the catalyst at the end of the reactor bank is replaced at a time different from the time when the catalyst is replaced in the reactors at the beginning of the reactor bank.

In the process of the present invention, the temperature of the feed is controlled such that during operation the outlet temperature of the final reactor is at least 4° C. higher than the outlet temperature of the first reactor. Preferably, the outlet temperature of the final reactor during operation is at least 8° C. higher than the outlet temperature of the first reactor. More preferably, the outlet temperature of the final reactor during operation is at least 10° C. higher than the outlet temperature of the first reactor, more preferably at least 15° C. higher. Most preferably, the outlet temperature of the final reactor during operation is at least 20° C. higher than the outlet temperature of the first reactor.

In the process of the present invention, the temperature of the feed is preferably controlled such that at the start of the operation the average temperature of each reactor is similar. Although there can be temperature differences, the difference in average temperature of the reactor having the highest average temperature and the reactor having the lowest average temperature is preferably at most 20° C., more preferably at most 15° C. There can be exceptional circumstances which make acceptable larger differences in average temperature. The average temperature is defined as sum of the temperature of the feed on entering the reactor and the temperature of the feed on leaving the reactor, and dividing the sum by 2.

Generally, catalyst deactivates during operation. Therefore, it is customary to increase the temperature of the reactor containing the catalyst. It has now further been found that a bank of reactors gives a higher yield if the temperature of the reactors is increased not only in such way that the outlet temperature of the final reactor is at least 4° C. higher than the outlet temperature of the first reactor but if additionally the average temperature of the first reactor is increased more slowly in time than the average temperature of the final reactor. Therefore, at the same point in time during operation the average temperature of the first reactor is lower than the average temperature of the final reactor. More preferably, the average temperature of the first and the final reactor is increased in time in such a way that the first reactor has a difference in average temperature between start of operation and a point in time during operation which is smaller than the same difference in average temperature of the final reactor at the same point in time during operation.

If the bank of reactors contains at least 5 reactors, it is preferred that the second reactor upstream of the final reactor is operated at an average temperature which is at least 5° C. higher during operation than the average temperature maintained in the first reactor, preferably at least 10° C. higher, more preferably at least 15° C. higher.

The temperature difference over reactors can differ greatly even if the average temperatures are similar. The temperature difference over a reactor will generally be determined by the feed composition, such as the amount of organic hydroperoxide present, the temperature of the feed on entering the reactor, the activity of the catalyst and the amount of catalyst present in the reactor. It will be clear that the latter can be chosen within the technical and economical constraints known to someone skilled in the art. The activity of the catalyst will depend strongly on the previous operation of the catalyst, such as the amount of feed treated, the number of hours in operation, the composition of the feed and the temperature at which the catalyst has been operated and is being operated. Preferably, the factors determining the temperature difference over a single reactor are maintained such that the temperature difference over the first reactor is smaller than the temperature difference over the final reactor. Preferably, the operation is carried out such that the temperature difference over the first reactor is at most 9° C. If the bank of reactors contains at least 3 reactors, it is further preferred that the temperature difference over the first reactor is smaller than the temperature difference over the middle one or two reactors. If the bank of reactors contains at least 5 reactors, it is preferred that operation is carried out such that the temperature difference over the second reactor upstream of the final reactor is larger than the temperature difference over the first reactor. If the bank of reactors contains at least 5 reactors, the temperature difference over the second reactor upstream of the final reactor preferably is at least 10° C. If the bank of reactors contains at least 5 reactors, the temperature difference over each the first and the second reactor most preferably is at most 9° C.

Catalyst is generally replaced when the operating temperature can not be increased further because the temperature of the product coming out of the reactor has reached the maximum temperature. The maximum temperature is mainly determined by the separation means to which the product is sent for separating off the alkylene oxide. The separation means will usually be a distillation column. At the same organic hydroperoxide conversion, increased yield has been observed if the outlet temperature of the final reactor is increased. It is preferred to allow the outlet temperature of the final reactor to be 125° C. or higher, more preferably 130° C. or higher, more preferably 135° C. or higher. Such a high outlet temperature of the final reactor allows reduction of the temperature of the preceding reactors. This allows the catalyst to be used to its full potential.

If cooling means are present between the final reactor and the reactor preceding the final reactor, it can be advantageous to operate the reactor preceding the final reactor at a higher average temperature than the final reactor such as shortly before the majority of the catalyst is to be replaced. In view of the temperature constraints due to the separation means behind the final reactor, the reactor before the final reactor is less restricted in its outlet temperature than the final reactor if cooling means are present between the reactors.

Heterogeneous epoxidation catalysts are known in the art. Such catalysts may comprise, as the catalytically active metal, one or more transition metals, such as vanadium, molybdenum, tungsten, titanium and zirconium. One particularly suitable class of heterogeneous epoxidation catalysts are the titanium-based catalysts. Examples of such catalysts are for instance described in U.S. Pat. No. 4,367,342 and EP-A-0,345,856. U.S. Pat. No. 4,367,342 discloses the use of inorganic oxygen compounds of silicon in chemical composition with at least 0.1% by weight of an oxide or hydroxide of titanium, while EP-A-0,345,856 discloses a titania-on-silica heterogeneous catalyst. According to EP-A-0,345,856 this catalyst is obtainable by impregnating a silicon compound with a stream of gaseous titanium tetrachloride followed by calcination and hydrolysis steps and optionally a silylation step.

In commercial operation, the average temperature in an epoxidation reactor is typically of from 50° C. to 150° C., preferably from 60° C. to 135° C. The pressure in each reactor can be up to 80 bar, preferably from 10 to 60 bar. Generally, the reaction medium is in the liquid phase.

In order to obtain the required temperature profile over each reactor, the feed is generally cooled with the help of cooling means present between two subsequent epoxidation reactors.

The bank of serially connected reactors, comprises at least 2 serially connected reactors. Preferably, the bank comprises of from 3 to 7 reactors.

In the process according to the present invention, the feed is preferably passed through the reactors of the bank in a fixed order. Therefore, the first reactor will remain the first reactor and the final reactor will remain the final reactor independent from the degree to which the catalyst has been deactivated.

Before passing the feed through a bank of reactors according to the present invention which bank is operated in a fixed order, at least part of the feed can have been passed through a series of reactors which is operated cyclically. A preferred series of reactors which can be used is a series of at least two serially connected reactors containing a bed of heterogeneous epoxidation catalyst particles and operated in a cyclic mode, optionally followed by at least one additional epoxidation reactor containing a bed of heterogeneous epoxidation catalyst particles, and continuously withdrawing a product stream from the final epoxidation reactor comprising alkylene oxide and an alcohol as reaction products, from which product stream the alkylene oxide end-product is recovered, in which process:

(a) the first reactor of the cyclically operated bank is put in a position further down this bank or in a position directly after any one of the additional reactors, when the activity of the epoxidation catalyst contained therein has decreased to an undesirably low level;

(b) in this position the catalyst with decreased activity is contacted with the effluent from the reactor in the preceding position at a temperature which is at least 5° C. higher than the final temperature at which the catalyst was in use in the first position of the bank and for sufficient time to restore its activity to the desired level.

This preferred series of reactors has been described in more detail in PCT patent application EP00/08052 which is hereby incorporated by reference.

The process according to the present invention is used in the reaction of an alkene with an organic hydroperoxide. Suitable organic hydroperoxides are secondary and tertiary hydroperoxides derived from a $C_4$-$C_{20}$ aliphatic hydrocarbon, a $C_7$-$C_{20}$ aralkyl hydrocarbon or mixtures thereof. Examples of suitable organic hydroperoxides include tert-butyl hydroperoxide, tertiary amyl hydroperoxide, tertiary octyl hydroperoxide, ethylbenzene hydroperoxide, cyclohexyl hydroperoxide and diethyl benzyl hydroperoxide. Of these, ethylbenzene hydroperoxide and tert-butyl hydroperoxide are most suitably applied.

The alkene used can be any organic compound having at least one aliphatic carbon-carbon double bond. Such compound will generally contain from 2 to 25 carbon atoms and preferably from 3 to 12 carbon atoms, such as propene, 1-butene, 2-butene, 1-pentene, 1-octene, 1-dodecene, styrene and methylstyrene. Most preferably, however, propene is used as the alkene, thus producing propylene oxide in accordance with the process of the present invention.

The heterogeneous epoxidation catalyst used may be any such catalyst known in the art to be suitable for catalysing the reaction between an alkene and an organic hydroperoxide into the corresponding alkylene oxide and alcohol. However, titanium-containing catalysts are preferred. Accordingly, the catalysts disclosed in the patent specifications U.S. Pat. No. 4,367,342 and EP-A-0,345,856 discussed above may, for instance, be applied. It has, however, been found particularly advantageous to use the titania-on-silica catalysts disclosed in EP-A-0,345,856 in all epoxidation reactors for the purpose of the present invention. When these catalysts are used, very good results are achieved by the present process.

A further catalyst which can be used in the process according to the present invention is a titanium-containing silicon oxide catalyst having (1) a mean pore size of at least 10 A, (2) 5 to 200 A pore size fraction constituting at least 90% of total pore volume, (3) specific pore volume of at least 0.2 cm$^3$/g, and (4) which catalyst is obtained by use of a quaternary ammonium salt template, followed by removal of the template, which template is $[NR^1R^2R^3R^4]^+$ (Within this formula, $R^1$ is a linear or branched hydrocarbon group having a carbon number of 2 to 36, and $R^2$ to $R^4$ indicate alkyl groups having carbon numbers of 1 through 6). The catalyst has been described in more detail in WO-A-01/5778 which is hereby incorporated by reference.

The product obtained in a process according to the present invention will generally contain at most 4% wt of unconverted organic hydroperoxide, preferably at most 2% wt, more preferably at most 1% wt. The amount of hydroperoxide which is converted in the final reactor can be quite small in which case there is sometimes only a small temperature difference over the final reactor.

The composition of the feed to the epoxidation reactor is not critical for the process of the present invention in the sense that it may have any composition which is common in commercial operation. Accordingly, in case of a styrene/propylene oxide co-production process, the feed to the epoxidation unit comprises at least some ethylbenzene hydroperoxide and normally also a substantial amount of ethylbenzene. Propene is either added to the reactor as a separate feed stream or may be added to the ethylbenzene hydroperoxide-containing feed stream prior to entry into the epoxidation reactor(s). The feed may also contain some methyl phenyl ketone and/or 1-phenyl-ethanol formed in the preceding oxidation section or in a preceding epoxidation reactor or contained in a recycle stream. The exact feed composition depends on whether at least part of the feed has already been contacted with a previous series of epoxidation reactors, preferably a series which is operated cyclically, preferably a series as described in patent application PCT/EP00/08052. A typical feed stream to the epoxidation reactor, which is first in line after the preceding oxidation step including oxidation reactor product work-up steps (like washing and distillation), comprises of from 15 to 25 wt % ethylbenzene hydroperoxide, of from 30 to 50 wt % ethylbenzene, of from 30 to 50 wt % propene, of from 0 to 5 wt % 1-phenyl-ethanol and of from 0 to 5 wt % methyl phenyl ketone, to a total of 100 wt %.

In an MTBE/propylene oxide co-production process the feed to the epoxidation reactor comprises at least some tert-butyl hydroperoxide (TBHP) in a tert-butanol solvent. Similar to the styrene/propylene oxide co-production process, propene is either added to the reactor as a separate feed stream or may be added to the TBHP-containing feed stream prior to entry into the epoxidation reactor.

The process according to the present invention can further comprise recovering the alkylene oxide from the product stream comprising alkylene oxide and an alcohol, preferably with the help of distillation.

The process according to the present invention can further comprise recovering the alcohol from the product stream comprising alkylene oxide and an alcohol and dehydrating the alcohol with the help of a dehydration catalyst to obtain the corresponding alkene.

The process according to the present invention can further comprise recovering the alcohol from the product stream comprising alkylene oxide and an alcohol and reacting the alcohol with methanol to obtain an ether.

The invention is further illustrated by the following examples without limiting the scope of the invention to these particular embodiments.

EXAMPLES

The epoxidation catalyst was a catalyst containing titanium on silica which was prepared as described in the Example according to the teaching of EP-A-345856.

The organic hydroperoxide used contained between 30 and 40% wt of ethylbenzene hydroperoxide in ethylbenzene.

There was a molar excess of propene present in the feed, based on the molar amount of organic hydroperoxide.

The feeds were supplied to the first reactor via two high pressure pumps and mixed together before entering the reactor. The reactor was operated liquid full at 50 bara pressure. Before entering the bank of reactors according to the present invention, the feed has been treated with the help of a series of reactors which is operated cyclically as described in patent application PCT/EP00/08052.

The bank of reactors consisted of 7 reactors which had been operated during more than 1 month. Each of these reactors contained at least 7% wt of the total amount of catalyst applied in the bank of reactors. Cooling means between each of the reactors adjusted the temperature of the reaction fluid, with the exception of reactors 6 and 7 between which there is no cooling means.

The product of reactor 7 was virtually free of ethylbenzene hydroperoxide both during operation according to the invention and during operation not according to the invention.

The propylene oxide yield was taken to be the molar amount of propylene oxide obtained divided by the molar amount of ethylbenzene hydroperoxide supplied, multiplied by 100.

Example 1

The temperature profile of the reactors was as described in Table 1 (not according to the invention).

TABLE 1

(not according to the invention)

| | Average temperature (° C.) | Temperature in (° C.) | Temperature out (° C.) | Increase (° C.) |
|---|---|---|---|---|
| Reactor 1 | 104 | 97 | 112 | 15 |
| Reactor 2 | 104 | 97 | 110 | 13 |
| Reactor 3 | 104 | 93 | 114 | 21 |
| Reactor 4 | 105 | 94 | 117 | 23 |
| Reactor 5 | 105 | 100 | 110 | 10 |
| Reactor 6 | 101 | 101 | 102 | 1 |
| Reactor 7 | 102 | 101 | 103 | 2 |

After changing the temperature profile over the reactors with the help of the cooling means, the temperature profile of Table 2 (according to the invention) was attained.

TABLE 2

(according to the invention)

| | Average temperature (° C.) | Temperature in (° C.) | Temperature out (° C.) | Increase (° C.) |
|---|---|---|---|---|
| Reactor 1 | 77 | 75 | 79 | 3 |
| Reactor 2 | 74 | 73 | 75 | 2 |
| Reactor 3 | 72 | 69 | 74 | 5 |
| Reactor 4 | 77 | 69 | 84 | 15 |
| Reactor 5 | 95 | 79 | 112 | 34 |

TABLE 2-continued (according to the invention)

| | Average temperature (° C.) | Temperature in (° C.) | Temperature out (° C.) | Increase (° C.) |
|---|---|---|---|---|
| Reactor 6 | 111 | 107 | 115 | 8 |
| Reactor 7 | 118 | 115 | 121 | 6 |

It was found that when operation was carried out according to Table 2 for 10 hours, the average propylene oxide yield during these 10 hours was 0.7 mole % higher than the average yield during the 10 hours before switching to the temperature profile according to Table 2, i.e. when the operation still had the temperature profile according to Table 1.

Example 2

After having operated the bank of reactors according to Table 2 for 3 days after having carried out Example 1, the temperature profile was according to Table 3 (according to the invention).

TABLE 3

(according to the invention)

| | Average temperature (° C.) | Temperature in (° C.) | Temperature out (° C.) | Increase (° C.) |
|---|---|---|---|---|
| Reactor 1 | 86 | 84 | 88 | 5 |
| Reactor 2 | 82 | 80 | 83 | 3 |
| Reactor 3 | 77 | 74 | 80 | 6 |
| Reactor 4 | 80 | 73 | 86 | 13 |
| Reactor 5 | 98 | 82 | 115 | 33 |
| Reactor 6 | 115 | 109 | 121 | 13 |
| Reactor 7 | 124 | 120 | 127 | 7 |

With the help of the cooling means, the temperature profile was changed to the temperature profile according to Table 4 (not according to the invention).

TABLE 4

(not according to the invention)

| | Average temperature (° C.) | Temperature in (° C.) | Temperature out (° C.) | Increase (° C.) |
|---|---|---|---|---|
| Reactor 1 | 105 | 99 | 111 | 12 |
| Reactor 2 | 103 | 98 | 108 | 10 |
| Reactor 3 | 103 | 95 | 111 | 17 |
| Reactor 4 | 103 | 93 | 113 | 20 |
| Reactor 5 | 101 | 94 | 108 | 13 |
| Reactor 6 | 109 | 108 | 111 | 4 |
| Reactor 7 | 112 | 110 | 114 | 4 |

It was found that when the operation according to Table 4 was carried out for 10 hours, the average propylene oxide yield during these 10 hours was 0.6 mole % less than the average propylene oxide yield during 10 hours before the temperature profile was changed to Table 4, i.e. during operation according to the temperature profile of Table 3.

Example 3

After having operated the bank of reactors not according to the invention for 4 days after having carried out Example 2, the temperature profile was according to Table 5 (not according to the invention).

TABLE 5

(not according to the invention)

| | Average temperature (° C.) | Temperature in (° C.) | Temperature out (° C.) | Increase (° C.) |
|---|---|---|---|---|
| Reactor 1 | 105 | 98 | 111 | 13 |
| Reactor 2 | 104 | 99 | 110 | 11 |
| Reactor 3 | 105 | 95 | 114 | 19 |
| Reactor 4 | 106 | 94 | 118 | 24 |
| Reactor 5 | 105 | 99 | 111 | 12 |
| Reactor 6 | 110 | 109 | 111 | 2 |
| Reactor 7 | 111 | 110 | 113 | 3 |

After changing the temperature profile over the reactors with the help of the cooling means, the temperature profile of Table 6 (according to the invention) was attained.

TABLE 6

(according to the invention)

| | Average temperature (° C.) | Temperature in (° C.) | Temperature out (° C.) | Increase (° C.) |
|---|---|---|---|---|
| Reactor 1 | 87 | 84 | 89 | 5 |
| Reactor 2 | 85 | 83 | 87 | 4 |
| Reactor 3 | 80 | 76 | 84 | 8 |
| Reactor 4 | 82 | 74 | 90 | 16 |
| Reactor 5 | 101 | 84 | 118 | 34 |
| Reactor 6 | 114 | 109 | 118 | 9 |
| Reactor 7 | 120 | 117 | 123 | 6 |

It was found that when operation was carried out according to Table 6 for 10 hours, the average propylene oxide yield during these 10 hours was 1.2 mole % higher than the average propylene oxide yield during 10 hours before switching to the temperature profile according to Table 6, i.e. when the operation still had the temperature profile according to Table 5.

Example 4

After having operated the bank of reactors according to the invention for 4 days, the temperature profile was according to Table 7 (according to the invention).

TABLE 7

(according to the invention)

| | Average temperature (° C.) | Temperature in (° C.) | Temperature out (° C.) | Increase (° C.) |
|---|---|---|---|---|
| Reactor 1 | 87 | 84 | 89 | 4 |
| Reactor 2 | 83 | 81 | 84 | 3 |
| Reactor 3 | 78 | 76 | 81 | 5 |
| Reactor 4 | 80 | 74 | 86 | 12 |
| Reactor 5 | 97 | 81 | 114 | 34 |
| Reactor 6 | 114 | 106 | 122 | 17 |
| Reactor 7 | 127 | 122 | 133 | 11 |

After changing the temperature profile over the reactors with the help of the cooling means, the temperature profile of Table 8 (according to the invention) was attained.

TABLE 8

(according to the invention)

| | Average temperature (° C.) | Temperature in (° C.) | Temperature out (° C.) | Increase (° C.) |
|---|---|---|---|---|
| Reactor 1 | 105 | 99 | 110 | 11 |
| Reactor 2 | 103 | 98 | 107 | 9 |
| Reactor 3 | 103 | 95 | 111 | 16 |
| Reactor 4 | 104 | 92 | 116 | 24 |
| Reactor 5 | 102 | 93 | 111 | 18 |
| Reactor 6 | 109 | 106 | 112 | 6 |
| Reactor 7 | 114 | 111 | 117 | 6 |

It was found that when operation was carried out according to Table 8 for 10 hours, the average propylene oxide yield during these 10 hours was 0.3 mole % less than the average propylene oxide yield during the 10 hours before switching to the temperature profile according to Table 8, i.e. when the operation still had the temperature profile according to Table 7.

We claim:

1. A process for the preparation of alkylene oxide, which process comprises: passing a feed containing an organic hydroperoxide and alkene through a bank of at least two serially connected reactors comprising a first reactor and a final reactor, each reactor containing a transition metal containing heterogeneous epoxidation catalyst and having an outlet temperature and an average temperature; and, withdrawing a product stream comprising alkylene oxide and an alcohol as reaction products, wherein the temperature of the feed is controlled in the bank of reactors such that during operation the outlet temperature of the final reactor is at least 4° C. higher than the outlet temperature of the first reactor and the average temperature of the first reactor is lower than the average temperature of the final reactor.

2. The process of claim 1, in which process the temperature difference over the first reactor is smaller than the temperature difference over the final reactor.

3. The process of claim 1, in which process the average temperature of the first and the final reactor is increased in time in such a way that the first reactor has a difference in average temperature between start of operation and a point in time during operation which is smaller than the difference in average temperature of the final reactor from the start of operation to the same point in time during operation.

4. The process of claim 1, in which process the feed is passed through the reactors of the bank in a fixed order.

5. The process of claim 1 further comprising passing at least part of the feed through a series of reactors which is operated cyclically, before passing the feed through a the bank of reactors operated in a fixed order.

6. The process of claim 1, which process further comprises recovering the alkylene oxide from the product stream comprising alkylene oxide and an alcohol.

7. The process of claim 1, which process further comprises recovering the alcohol from the product stream comprising alkylene oxide and an alcohol and dehydrating the alcohol with a dehydration catalyst to obtain the corresponding alkene.

8. The process of claim 1, which process further comprises recovering the alcohol from the product stream comprising alkylene oxide and an alcohol and reacting the alcohol with methanol to obtain an ether.

9. The process of claim 2, in which process the average temperature of the first and the final reactor is increased in time such that the first reactor has a difference in average temperature from start of operation and a point in time in operation which is smaller than the difference in average temperature of the final reactor from start of operation and the same point in time during operation.

10. The process of claim 2, in which process the feed is passed through the reactors of the bank in a fixed order.

11. The process of claim 2, which process further comprises recovering the alkylene oxide from the product stream comprising alkylene oxide and an alcohol.

12. The process of claim 2, which process further comprises recovering the alcohol from the product stream comprising alkylene oxide and an alcohol and dehydrating the alcohol with a dehydration catalyst to obtain the corresponding alkene.

13. The process of claim 2, which process further comprises recovering the alcohol from the product stream comprising alkylene oxide and an alcohol and reacting the alcohol with methanol to obtain an ether.

14. The process of claim 3, in which process the feed is passed through the reactors of the bank in a fixed order.

15. The process of claim 3, which process further comprises recovering the alkylene oxide from the product stream comprising alkylene oxide and an alcohol.

16. The process of claim 4, in which process the feed is passed through the reactors of the bank in a fixed order.

17. The process of claim 4 further comprising passing at least part of the feed through a series of reactors which is operated cyclically, before passing the feed through the bank of reactors operated in a fixed order.

18. The process of claim 4, which process further comprises recovering the alkylene oxide from the product stream comprising alkylene oxide and an alcohol.

19. The process of claim 5, which process further comprises recovering the alkylene oxide from the product stream comprising alkylene oxide and an alcohol.

20. The process of claim 5, which process further comprises recovering the alcohol from the product stream comprising alkylene oxide and an alcohol and reacting the alcohol with methanol to obtain an ether.

* * * * *